United States Patent [19]

Fuchs et al.

[11] Patent Number: 5,759,586
[45] Date of Patent: Jun. 2, 1998

[54] PHARMACEUTICAL OR DIETETIC COMPOSITION

[76] Inventors: Norbert Fuchs, 135 Bruckdorf, A-5571 Mariapfarr; Norbert Zelch, 11a Wasserfeldstrasse, A-5020 Salzburg; Peter Koessler, 219 Bruckdorf; Rupert Loidl, Tischlerhaeusl, both of A-5571 Mariapfarr, all of Austria

[21] Appl. No.: 725,301

[22] Filed: Oct. 2, 1996

[30] Foreign Application Priority Data

Jul. 19, 1996 [AU] Australia ................ A1304/96

[51] Int. Cl.$^6$ ........................................ A61K 33/06
[52] U.S. Cl. ................ 424/686; 424/715; 424/717; 514/167; 514/474
[58] Field of Search ..................... 424/686, 715, 424/717; 514/167, 474

[56] References Cited

U.S. PATENT DOCUMENTS

| | | | |
|---|---|---|---|
| 3,993,750 | 11/1976 | Fox, Jr. ................ | 424/128 |
| 3,993,751 | 11/1976 | Zinke ................ | 424/128 |
| 4,582,709 | 4/1986 | Peters et al. ................ | 426/74 |
| 4,634,591 | 1/1987 | Westerman ................ | 424/149 |
| 5,114,723 | 5/1992 | Stray-Gundersen ................ | 426/74 |
| 5,158,944 | 10/1992 | Makino et al. ................ | 514/167 |

FOREIGN PATENT DOCUMENTS

| | | |
|---|---|---|
| 307620 | 5/1973 | Austria. |
| E16565B | 5/1986 | Austria. |
| 0217975A1 | 4/1987 | European Pat. Off.. |
| 0353065A1 | 1/1990 | European Pat. Off.. |
| 0374935A1 | 6/1990 | European Pat. Off.. |
| 3943424A1 | 7/1991 | Germany. |
| WO90/04402 | 5/1990 | WIPO. |
| WO91/04018 | 4/1991 | WIPO. |

*Primary Examiner*—Kevin E. Weddington
*Attorney, Agent, or Firm*—Arnold, White & Durkee

[57] ABSTRACT

There is disclosed a pharmaceutical or dietetic composition, comprising
  sodium, potassium, magnesium and calcium ions, wherein at least sodium and potassium are present as carbonates and/or bicarbonates, and
  enzyme activators,
the mass ratio of K:Ca:Na:Mg being 0.1–100:0.05–80:0.03–50:1, the composition containing at least 40 mmol of alkaline or alkalizing ions and the composition, dissolved in water, having a pH of $\geq 7.5$.

30 Claims, No Drawings

PHARMACEUTICAL OR DIETETIC COMPOSITION

The invention relates to pharmaceutical or dietetic compositions which preferably may be used for the prevention and treatment of osteoporosis.

The term osteoporosis is derived from the Greek words "osteon" and "poros", respectively, and was first introduced by pathologists at the end of the 19th century.

It was intended to distinguish this generalized bone disease from the bone diseases such as osteomalacia and ostitis fibrosa cystica very frequently occurring at that time. It was the endocrinologist Fuller Albright who first defined osteoporosis pathologically unambiguously as a condition "in which there is a lack of bone tissue but this bone tissue remains fully calcified". Today, osteoporosis is mostly defined as a loss or reduction of bone substance, structure and function, which leads to an increased fracture incidence, or as a generalized disease of the skeleton, which is characterized by a low bone mass and an impaired microarchitecture of the bone tissue, leading to an increased brittleness of the bones and to an increase risk of fracture.

The various forms of osteoporosis may be classified according to different criteria, e.g., according to etiology, according to the pattern of distribution of the osteoporosis, or according to metabolic criteria.

According to etiology, it is differentiated between primary osteoporoses of undetermined origin and secondary osteoporoses due to endocrinal, metabolic or other known causes (Table 1).

The primary osteoporoses include the idiopathic osteoporosis, where, depending on the time of life in which it occurs, one differentiates between juvenile osteoporosis (up to 18 years), idopathic osteoporosis in early adult age (up to 50 years); the post-climacteric or post-menopausal osteoporosis (50 to 70 years) probably also caused by the climacteric estrogen decrease (thus, also the term estrogen deficiency osteoporosis), and senile osteoporosis (as of 70 years) caused by multiple factors.

TABLE 1

Classification of Osteoporosis According to Etiology (Including Examples)

I. Primary Osteoporosis
 a) idiopathic osteoporosis
 b) post-climacteric osteoporosis (type I)
 c) senile osteoporosis (type II)

II. Secondary Osteoporosis
 a) Endocrinologically/metabolically caused osteoporosis (Cushing syndrome, hyperthyreosis, hypogonadism, hyperparathyreoidism)
 b) iatrogenically caused osteoporosis, osteoporosis caused by medicaments (glucocorticoids, heparin)
 c) within the frame of complex osteopathies (gastro-enterological causes (false nutrition, malabsorption, malassimilation), special forms of renal osteopathy)
 d) within the frame of neoplastic diseases (multiple myeloma, lympho and myeloproliferative aberrations)
 e) hereditary diseases of the connective tissue (osteogenesis imperfecta, Marfan syndrome, Ehlers-Danlos syndrome)
 f) reduction of the static forces on the bone (bed rest, paraplegia, weightlessness)

Osteoporosis may also be classified into various types on account of its pattern of distribution (Table 2).

TABLE 2

Pattern of Distribution of Osteoporosis

A.: Generalized Osteoporosis
 Type I: Spongiosa-emphasized loss of bone mass, manifestation on the original skeleton by fractions of vertebral bodies (post-climacteric osteoporosis)
 Type II: Generalized loss of bone mass (with respect to both, spongiosa and compacta), manifestation on long tubular bones by fracture of the neck of the femur, radius fracture (senile osteoporosis).
B.: Localized, asymmetric osteoporosis (M. Sudeck)

When classifying according to metabolic criteria, it is distinguished between high turn-over osteoporosis (spontaneously starting, rapid bone loss) and low turn-over osteoporosis (slow bone loss).

High turn-over osteoporosis is mainly found in type I or post-climacteric osteoporosis and in idiopathic osteoporosis in early adulthood. A rapid bone mineral loss ("fast loser"; bone mineral loss of more than 3.5% within one year) generally initiates the active phase of the osteoporosis.

Among the low turn-over osteoporoses there are the type II or senile osteoporoses.

So far, the causes giving rise to osteoporosis have not yet been clarified, yet the calcium theory, the estrogen deficiency theory and the cellular theory are mainly under discussion.

According to the calcium theory, the causes giving rise to osteoporosis are a bone or calcium metabolism disorder as a consequence of a lack of calcium in nutrition, gastrointestinal malabsorption or increased excretion via the kidneys.

The estrogen deficiency theory says that an osteoporosis occurs in women with an individual disposition as a consequence of the reduced estrogen production occurring after menopause.

According to the cellular theory it is assumed that osteoporosis occurs as a consequence of a disorder of the bone formation caused by an ageing of the osteoblasts. Primary osteoporosis with an increased osteoclast activity is said to be connected with a disturbance of the negative feedback between the calcium concentration in the serum and the parathormone secretion from the parathyroid glands.

For the therapy of osteoporosis, at present substantially the following therapeutic measures are used:

1. therapeutic agents inhibiting bone resorption
2. therapeutic agents stimulating bone formation
3. positivation of the calcium balance
4. symptomatic pain treatment
5. physical therapy The main therapeutic aim of the treatment of osteoporosis is a reduction of the fracture rate by stabilizing or raising the mineral content of the skeleton above the clinical manifestation or fracture limit. At present, already a stopping of the decrease of the mineral content of the skeleton and freedom from pain are seen as a success of therapy.

As the therapeutic agents inhibiting bone resorption, estrogens, calcitonin and biphosphonate derivatives are most frequently used.

Estrogens can prevent the rapidly starting post-menopausal bone loss, yet only as long as the supply of estrogens lasts. The mechanism by which estrogens act is still unknown. What is clear is only that the osteoclast activity is inhibited by this hormone. Protection of the skeleton requires an estrogen substitution for several (at least seven) years.

For the therapy of post-menopausal osteoporosis, estrogen/gestagen combination preparations are mainly used, since thereby the estrogen-induced risk of a carcinoma of the endometrium can be reduced. An estrogen substitution is particularly indicated in the preclinical stage of osteoporosis—type I, since here the bone loss of the "fast loser" can be braked.

The peptide hormone calcitonin is produced in the C cells of the thyroid gland and acts as an inhibitor of the osteoclast function, while the osteoblasts are not influenced. The centrally analgesic action of calcitonin is of advantage, yet only about 50% of the patients react thereto. A therapy period of six weeks is recommended, and the treatment is to be stopped as being unsuccessful if there is no improvement within the first two weeks. The disadvantage of a calcitonin therapy is that this neurohormone can only be administered parenterally due to its peptide character.

Bisphosphonates inhibit skeleton resorption, and have successfully been used in case of rapid skeleton loss. Derivatives of pyrophosphate (etidronic acid, cladronic acid) offer a number of advantages, such as a long half-life in the bone, which allows a compliance-promoting intermittent therapy, and oral efficacy.

As the therapeutic agents stimulating bone formation, parathormone, anabolics and fluorides are mainly used.

As regards its physiologic activity, parathormone would be suitable to stimulate bone formation, yet so far too little experience has been gathered to form a competent judgment.

An anabolic steorid for the treatment of manifest osteoporosis is nandrolone decanoate, e.g. The effect of nandrolone decanoate is based on multiple factors. Inter alia, a stimulation of the periostal growth by making positive the nitrogen balance is under discussion. On the whole, an increase in the bone mass as well as an improved calcium resorption are obtained by nandrolone decanoate.

Fluorides promote the new bone formation by stimulating the osteoblasts. Under the influence of fluorides, the osteoblasts increasingly form a matrix of collagen in which fluoride apatite is then incorporated. What must be taken into consideration is that the matrix formation precedes the mineralization process in terms of time so that the bone is capable of bearing a respective load only at a relatively late point of time. It is appropriate to supplement the fluoride therapy with an administration of calcium and vitamin D, since a combination therapy promotes the incorporation of mineral salts in the matrix bone.

Calcium metabolism plays a central role in the etiology, pathogenesis and therapy of osteoporosis. In the human organism, approximately 1,000 to 1,500 g of calcium are stored, 99% thereof being in the skeleton. To equalize the daily loss, the calcium uptake should be between 700 and 1,000 mg per day (depending on age).

The present invention is based on the object of providing a completely new possibility of treating osteoporosis which not only enables the symptomatic treatment or stabilization of osteoporosis patients, but also counteracts the causes of osteoporosis.

This object is achieved by a pharmaceutical or dietetic composition comprising
sodium, potassium, magnesium and calcium ions, at least sodium and potassium being present as carbonates and/or bicarbonates, and
enzyme activators,
the quantitative ratio of K:Ca:Na:Mg being 0.1–100:0.05–80:0.03–50:1, the composition containing at least 40 mmol of alkaline or alkalizing ions (with respect to the daily dose), and the composition dissolved in water having a pH of $\geq 8.0$.

The mode of action of this preparation is based on alternative approaches regarding the formation of osteoporosis, i.e. by regarding the formation of osteoporosis from the point of view of the acid-base balance, and on the system of the basic regulation with a view to the formation of osteoporosis:

To maintain a constant pH, which is different depending on the compartment, several buffer systems (blood, connective tissue, kidneys, lungs IZR, EZR) are available to the body. False nutrition over several years, suboptimum micro nutrient supply as well as physical and emotional stress factors exhaust the neutralizing capacity of the body's own regulation systems, thus inducing a shift to the left (acidoses) or a shift to the right (alkaloses) in the acid-base balance.

The consequences of a shift to the left of the acid-base balance are lesions of the connective tissue caused by acids (tissue acidoses), which are seen as essential causes of civilization diseases, such as cardiac infarction, osteoporosis, rheumatism and gout.

Among the causative agents of such an "overacidification of the tissue" there are non-volatile metabolites which are formed from acid-forming nutritional components (refined carbohydrates, animal proteins, coffee) with a simultaneous nutrition poor in alkali. The acids formed by intermediary metabolic processes are taken up by the blood, neutralized, and eliminated from the body via pulmonary breathing off ($CO_2$) and renal excretion.

The neutralization of acids via the blood buffer system is, however, only possible within the frame of its buffer capacity (narrow working pH!). Excessive acid is removed into the interstitium, buffered, and intermediately stored until it is further transported off via the blood (if buffer capacities are free) and the kidneys. A direct secretion of substances from the connective tissue is not possible because of the lack of direct secretion possibilities.

Acidotic metabolic conditions lead to a withdrawal of alkaline salts from the body. As a consequence, the mobilization of calcium, magnesium and phosphate (alkaline salts) from the bones increases, which alltogether leads to a demineralization of the skeleton.

Even a sufficient calcium supplementation cannot stop the demineralization process, since the absorbed calcium immediately is withdrawn to neutralize the acids and thus never becomes available for an incorporation into the skeleton.

As a further aspect in the formation of acid metabolic conditions with an increased calcium mobilization from the bones, an accumulation of homotoxines (acid character) in menopausal women according to the homotoxin teaching of Reckeweg is under discussion.

The system of the basic regulation is defined (according to Pischinger) as a functional unit of the vessel end flow path, the connective tissue cells and the vegetative-nervous end formation. The common action and information principle of this trias is the extracellular fluid. Lymphatic vessels and lymphatic organs are connected therewith. The connective tissue embedded in the extracellular fluid thus is the largest and single system extending through the entire body which is in direct contact with each body cell.

Biochemically, the basic substance (extracellular matrix) forms a network (molecular sieve) consisting of polysaccharides which are partially bound to protein (proteoglycans and glycosamino glycans (PG/GAGs), as well as structure and cross-linking proteins (collagen, elastin, fibronectin and others). Functional aspects of the extracellular matrix are transmitter, storage and regulation tasks.

The transmission of molecules is closely connected with the molecular sieve structure of the basic substance, the pore size of the "filter" being dependent on the concentration and quality of the dissolved proteoglycans, their molecular weights, the pH of the solution and the electrolytes present (dissolved bulk and trace elements) in the respective tissue region.

Endogenous malformations (hereditary or age-caused accumulations of genetic mistakes and errors of the cellular control mechanisms) or exogenic factors (environmental loads, chemical radicals, false nutrition, stress, viral and bacterial infections, radiation, alkylating substances) influence all the steps of synthesis and metabolism of the structural components of the basic substance (restriction of the function of the basic substance!), whereby i.a. the large number of connective tissue, vessel, cartilage and bone disorders is brought about.

With increasing age, unphysiological changes of the basic substance increasingly occur ("slagging"). The bonding of heavy metal ions, antigen antibody complexes and defective proteins to PG/GAGs, non-enzymatic glycosilations of sugar-containing substances and the thickening of the basal membrane are characteristics of such slagging and on the whole impede the cellular supply and removal and lead to tissue hypoxias which in turn encourage the formation of general acidoses.

On the whole, slagging and the occurrence of acidoses on the one hand cause a reduced nutrient supply to the bone cells (due to unphysiological structural changes of the basic substance), and, on the other hand, a withdrawal of basic ions from the skeleton (to compensate acidotic tendencies).

The compositions of the present invention obtain a marked improvement in bone mineralization by means of a well-balanced supply of the important elements sodium, potassium, calcium and magnesium, as well as optionally further essential macro and micro elements over an extended period of time. What is decisive in this connection is that the above-mentioned electrolytes are present as being bound to alkaline or alkalising anions, such as carbonates, bicarbonates, citrates, gluconates, tartrates or lactates.

Thus an increase of the buffer capacities of extra and intracellular spaces, in particular of the connective tissue, is enabled by basic cations and anions (i.e. by an equalization of azidotic tendencies by the purposeful use of alkaline compounds), wherein the filter or molecular sieve function of the "basic substance" and thus an increased transmission of micronutrients are regenerated.

The composition according to the invention preferably comprises further substances, e.g. skeleton substances, preferably on the basis of silicon, and/or additives or auxiliary substances, preferably carbohydrates and/or aromatics.

These substances serve both to improve the effect of the composition and to complete it to a product ready for sale. As additives, i.a. carbohydrates, such as fructose, sucrose or starch, natural aromas and aromas identical to natural aromas or other flavours are being considered.

As enzyme activators, preferably the bulk and trace elements are used which are essential to the human body or are especially required in osteoporosis appearances. Examples of such enzyme activators are Li, Sr, Zn, Fe, Mn, Cu, Cr, Mo, Se, F ions, vitamins, preferably vitamin C, K and $D_3$, as well as mixtures of such enzyme activators.

The preferred anions which can be used in the composition according to the invention are, e.g., carbonate, hydrogen carbonate, glycerophosphate, pyrophosphate, gluconate, citrate, ascorbate, lactate, molybdate, chloride and phosphate.

When determining the preferred quantitative ratio, the individual requirements of the patient or (in case of prevention) of the healthy individual have to be aimed at in addition to the known values of daily requirement or ratios. Preferably, the composition according to the invention thus contains potassium, calcium, sodium and magnesium at a quantitative ratio of 0.5–20:0.2–16:0.1–10:1, in particular of 1–10:0.5–8:0.3–5:1, the electrolytes mentioned being present as bound to alkaline or alkalizing anions (with a total amount of at least 40 mmol).

The dose to be administered should be as close as possible to the individual demand of the respective patient. As a rule, treatment and prevention will be carried out with the average dose of daily demand which may be exceeded or fallen below, if required (e.g. by the factor 3 or ⅓).

In case of a normal daily demand, as a rule a quantitative ratio of K:Ca:Na:Mg of approximately 5:2.5:1.5:1 is sufficient.

In solution, the composition according to the invention must have an alkaline pH, preferably in the range of from 7.5 to 9.5, more preferably 8.9 to 9.0.

When using the composition according to the invention as a medicament, it should be present in a pharmaceutically administrable formulation, the formulation for administration preferably being an oral or a parenteral form of administration. More details regarding suitable pharmaceutical formulating substances (depending on the type of administration or dose) will be known to the skilled artisan in this field and can be taken from the pharmacopoeia.

The composition according to the invention may also be used as a foodstuff or as an additive to a foodstuff, and again known additives or carriers suitable in terms of foodstuff technology can be combined with the composition into a formulation suitable in terms of foodstuff technology.

A further aspect of the present invention relates to the composition according to the invention as a medicament.

Furthermore, the present invention relates to the use of the composition according to the invention for producing a preparation for the prevention and treatment of acidotic diseases.

Subject matter of the invention is, of course, also the use of the composition according to the invention for producing a preparation for the prevention and treatment of osteoporosis, i.e. all types of osteoporosis (cf. Tables 1 and 2), wherein in particular the widely distributed primary osteoporosis and the generalized osteoporosis are in the foreground, as well as the stimulation of bone mineralization and the build-up of the organic bone matrix after bone fractures.

Furthermore, the composition according to the invention can be used for the production of a preparation for the regeneration of the ionic balance, in particular in the cells of the connective tissue, as well as for the production of a preparation for the stabilization and improvement of bone density, in particular the bone mass and the mineral density of bones.

The invention will be explained in more detail by way of the following examples, to which, however, it is not limited.

EXAMPLES

1. Diagnostics 1.1. Radiodiagnostics

In osteoporosis, typical radiological changes on the spine are an increased radiation permeability with enlarged trabecula distances, deformation of the vertebrae in the form of wedge-shaped vertebrae, platyspondylia, and fish vertebrae. X-ray examination is, however, not useful in the early diagnosis of osteoporosis, because osteoporosis is radiologically clearly recognizable only at a bone mineral loss of more than 30–40%. Thus, this method is only used to diagnose the manifest osteoporosis when fractures have already occurred.

1.2. Measurements of Bone Density (osteodensitometry)

1.2.1. Quantitative computerised tomography (QCT)

Quantitative computerised tomography (QCT) is very useful for a selective density determination of spongiosa and compacta. Principle: By aid of special software and calibration phantoms, the bone mineral content is determined from the decrease of X-ray radiation in a defined area of the examined body.

Duration of measurement: 10 to 20 min
Radiation load: 50 to 500 mrem
Reproduction errors: 3 to 10%

Measurement errors result from the fat content of the bone marrow in the so-called fat-containing or yellow bone marrow. In QCT, the reproducibility of the results decisively depends on whether or not in examination repeats the measured organ is exactly hit again. Shifts of 1 mm may already cause errors of 1%.

1.2.2. Peripheral Quantitative Computerised Tomography (pQCT)

Principle: The bone is analysed by aid of an automatic shape recognition, and the hydroxy apatite equivalent (HE) is determined in the volume, whereby it is possible to separately determine the HE in compacta and spongiosa. Since pathological-metabolic bone changes mostly are generalized system diseases, measurement at points of reference at which there are hardly any secondary changes are necessary.

1.2.3. Single Energy Photon Absorptiometry, SPA

SPA is used to determine the local bone mineral content in the peripheral skeleton (forearm, calcaneus). Principle: Monoenergetic gamma radiation is emitted from a radiation source ($^{125}$Iodine), which penetrates the patient's body. A direct conclusion can be drawn from the intensity decrease of the photon ray to the mineral salt content of the bone.

Duration of examination: 15 to 20 min
Radiation load: 2 to 5 mrem
Reproduction error: 2%

Measurement errors result from the absorption of the rays in the soft tissue.

1.2.4 Dual Energy Photon Absorptiometry, DPA

DPA is mainly used to measure the bone mineral content of the rather spongy bone of the lumbar spine and of the proximal femur. Principle: In this method, radioactive substances (primarily $^{135}$ gadolinium emitting monochromatic radiation with two energy maximums serve as the radiation source. This radiation decreases when passing through tissue, the radiation decrease mainly being determined by the bone mineral content.

Due to the different absorption rates of the two monoenergetic photon energies in soft tissue and in bone, it is possible to determine the bone mineral salt content without soft tissue error.

Duration of examination: 30 min
Radiation load: 2 to 3 mrem
Reproduction error: 2%

In this method, a special source of error resides in the exhaustion of the radiation source, whereby the emitted radiation quality changes.

1.2.5. Dual Energy X-Ray Absorptiometry, DXA

Other names of this method are also DPX (Dual Photon X-Ray Absorptiometry, DEXA (Dual Energy X-Ray Absorptiometry) or QDR (Quantitative Digital Radiography). Principle: Instead of radioactive substances, DXA, a further development of DPA, uses an X-ray tube as the radiation source, which works with two radiation maxima, analogous to DPA. The bone mass is determined via the hydroxy apatite equivalent (HE) in the lumbar spine.

Duration of examination: 5 min
Radiation load: 0.5 to 3 mrem
Reproduction error: 1%

Determination errors of the bone mineral content may occur as a consequence of changes on the vertebral bodies, such as scoliosis, grave degenerative changes or also after vertebral fractures. As further sources of determination errors, occurring sponylarthroses, spondylophytes, calcifications in lymph nodes or vessels are to be seen, provided these structures are in the field measured, and X-ray contrast materials present within the body because of other examinations. To reduce these errors, a conventional X-ray image is always additionally required in case of a DXA measurement. Taking into consideration the radiation load, DXA is considered the method of choice, particularly with comprehensive and repeated measurements on postmenopausal women, for informative screenings as well as for checks on the development of disease and on therapy.

2. Preparation of the Compound

A compound according to the invention was prepared from sodium (mainly as the hydrogen carbonate), potassium (mainly as the carbonate and citrate), magnesium (mainly as the carbonate) and calcium salts (mainly as the carbonate and chloride) by mixing the same, comprising 800 mg K, 400 mg Ca, 250 mg Na and 150 mg Mg.

The ingredients were as follows: fructose, starch, potassium carbonate, magnesium citrate, natural and nature-identical aromas, calcium carbonate, sodium hydrogen carbonate, diatomaceous earth, calcium chloride, magnesium carbonate, potassium citrate, calcium glycerophosphate, sodium pyrophosphate, sodium ascorbate, iron gluconate, manganese gluconate, zinc gluconate, selenium yeast, strontiumlactate, copper gluconate, lithium carbonate, sodium fluoromonophosphate, chromium trichloride hexahydrate, sodium molybdate, phytomenadione, cholecalciferene.

Thus, this composition had the following bulk and trace elements:

silicone 129.90 mg
chloride 120.40 mg
phosphorus 35.75 mg
manganese 5.55 mg
iron 5.55 mg
zinc 5.55 mg
strontium 5.55 mg
lithium 1.10 mg
copper 1.10 mg
fluorine 550.00 µg
chromium 111.00 µg
molybdenum 111.00 µg
selenium 55.50 µg
vitamins C 55.60 mg
K 30.00 µg
$D_3$ 3.00 µg 3. Administering the Preparation According to the Invention The preparation produced in Example 2 was stirred into ¼ l of water (pH=8.96) or vegetable juice (non-$CO_2$- containing mineral water or fruit juices and other acid-containing soft drinks) twice a day and taken after the meals.

To examine the efficacy of the agent according to the invention for treating post-climacteric osteoporosis, the female patients were subdivided into several examination groups:

Group 1: without therapy (15 female patients)
Group 2: oral hormone therapy (15 female patients)
Group 3: treatment with the agent according to the invention (20 female patients)
Group 4: treatment with the agent according to the invention plus treatment with hormones (18 female patients)

Group 1 represents the comparative value without any treatment; Group 2 receives a treatment according to the prior art; Group 3 receives the treatment with the preparation according to the invention; and Group 4 the combination of the preparation according to the invention with a treatment according to the prior art.

The results are listed in Tables 3 to 6 and show clearly that, surprisingly, with the composition according to the invention the best values in the change of bone density (determined by means of the DXA method on the spine and on femur/thigh, respectively could be obtained in the treatment period between the first and the second measurements (approximately 12 months) (average of +2.88%). With the oral hormone therapy according to the prior art, the bone density could be increased by an average of +1.85%, with the combination of a hormon therapy and the composition according to the invention the increase was still +1.66%. In contrast thereto, the bone density of untreated female patients decreased by 3.47% in the comparative period.

TABLE 3

Group 1: Without therapy (15 femal patients)

| Nr. | Initials | Pat. Nr. | Group | Age | Menopause at | Bone Density in % 1. Measuremt | Bone Density in % 2. Measuremt. | Change | Change in % |
|---|---|---|---|---|---|---|---|---|---|
| 1 | A. Z. | 1298 | 1 | 72 | 49 | 99 | 98 | −1 | −1.01% |
| 2 | H. H. | 1668 | 1 | 69 | 49 | 148 | 148 | 0 | 0.00% |
| 3 | I. G. | 711 | 1 | 49 | 49 | 105 | 105 | 0 | 0.00% |
| 4 | G. M. | 1619 | 1 | 74 | 53 | 90 | 90 | 0 | 0.00% |
| 5 | L. H. | 1730 | 1 | 55 | 52 | 92 | 91 | −1 | −1.09% |
| 6 | M. S. | 1643 | 1 | 73 | 47 | 88 | 87 | −1 | −1.14% |
| 7 | E. D. | 413 | 1 | 52 | 50 | 109 | 106 | −3 | −2.75% |
| 8 | J. S. | 1878 | 1 | 71 | 54 | 90 | 86 | −4 | −4.44% |
| 9 | R. T. | 1578 | 1 | 48 | 48 | 115 | 103 | −12 | −10.43% |
| 10 | H. B. | 1316 | 1 | 54 | 47 | 84 | 83 | −1 | −1.19% |
| 11 | V. Z. | 1557 | 1 | 47 | 44 | 120 | 117 | −3 | −2.50% |
| 12 | E. E. | 1465 | 1 | 46 | 46 | 94 | 94 | 0 | 0.00% |
| 13 | I. L. | 186 | 1 | 50 | 50 | 77 | 73 | −4 | −5.19% |
| 14 | H. W. | 1660 | 1 | 62 | 52 | 126 | 102 | −24 | −19.05% |
| 15 | E. W. | 1702 | 1 | 51 | 52 | 117 | 117 | 0 | 0.00% |
| | Mean: | | | 58.2 | 49.47 | 103.6 | 100 | −3.6 | −3.47% |
| | Standard deviation: | | | 10.70 | 2.80 | 18.97 | 18.05 | 6.43 | |

TABLE 4

Group 2: Oral hormone therapy (15 female patients)

| Nr. | Initials | Pat. Nr. | Group | Age | Menopause at | Bone Density in % 1. Measuremt | Bone Density in % 2. Measuremt. | Change | Change in % |
|---|---|---|---|---|---|---|---|---|---|
| 1 | R. S. | 1428 | 2 | 54 | 52 | 92 | 99 | 7 | 7.61% |
| 2 | I. W. | 1725 | 2 | 56 | 48 | 88 | 91 | 3 | 3.41% |
| 3 | U. B. | 1570 | 2 | 38 | 32 | 116 | 114 | −2 | −1.72% |
| 4 | W. W. | 1544 | 2 | 51 | 51 | 99 | 96 | −3 | −3.03% |
| 5 | E. K. | 1312 | 2 | 52 | 50 | 107 | 112 | 5 | 4.67% |
| 6 | B. G. | 486 | 2 | 62 | 53 | 103 | 103 | 0 | 0.00% |
| 7 | B. H. | 1022 | 2 | 43 | 43 | 89 | 88 | −1 | −1.12% |
| 8 | F. F. | 1161 | 2 | 53 | 50 | 119 | 119 | 0 | 0.00% |
| 9 | E. R. | 698 | 2 | 52 | 50 | 64 | 74 | 10 | 15.63% |
| 10 | P. I. | 462 | 2 | 51 | 49 | 114 | 116 | 2 | 1.75% |
| 11 | H. F. | 1302 | 2 | 54 | 50 | 88 | 89 | 1 | 1.14% |
| 12 | H. I. | 2544 | 2 | 54 | 50 | 76 | 77 | 1 | 1.32% |
| 13 | H. K. | 1534 | 2 | 66 | 55 | 74 | 77 | 3 | 4.05% |
| 14 | M. L | 1652 | 2 | 76 | 56 | 88 | 87 | −1 | −1.14% |
| 15 | W. K. | 1485 | 2 | 64 | 57 | 90 | 91 | 1 | 1.11% |
| | Mean: | | | 55.40 | 49.73 | 93.80 | 95.53 | 1.73 | 1.85% |
| | Standard deviation: | | | 8.81 | 5.98 | 15.95 | 14.67 | 3.47 | |

TABLE 5

Group 3: Treatment with preparation according to the invention (20 female patients)

| Nr. | Initials | Pat. Nr. | Group | Age | Menopause at | Bone Density in % 1. Measuremt | Bone Density in % 2. Measuremt | Change | Change in % |
|---|---|---|---|---|---|---|---|---|---|
| 2 | M. S. | 1888 | 3 | 80 | 52 | 90 | 93 | 3 | 3.33% |
| 4 | S. A. | 1776 | 3 | 78 | 49 | 77 | 77 | 0 | 0.00% |
| 5 | T. F. | 1910 | 3 | 86 | 52 | 93 | 94 | 1 | 1.08% |
| 6 | C. C. | 1912 | 3 | 71 | 46 | 79 | 80 | 1 | 1.27% |
| 7 | M. H. | 1928 | 3 | 74 | 36 | 69 | 71 | 2 | 2.90% |
| 9 | L. C. | 1601 | 3 | 72 | 52 | 75 | 84 | 9 | 12.00% |
| 11 | E. C. | 1822 | 3 | 86 | 52 | 54 | 60 | 6 | 11.11% |
| 13 | S. M. | 2032 | 3 | 79 | 41 | 66 | 68 | 2 | 3.03% |
| 14 | M. E. | 2048 | 3 | 70 | 48 | 70 | 69 | -1 | -1.43% |
| 18 | A. F. | 1427 | 3 | 67 | 38 | 69 | 72 | 3 | 4.35% |
| 20 | C. K. | 1463 | 3 | 60 | 27 | 88 | 88 | 0 | 0.00% |
| 21 | M. G. | 2055 | 3 | 66 | 48 | 97 | 99 | 2 | 2.06% |
| 23 | M. F. | 1841 | 3 | 72 | 49 | 84 | 85 | 1 | 1.19% |
| 25 | P. N. | 2153 | 3 | 69 | 50 | 76 | 77 | 1 | 1.32% |
| 27 | M. K. | 2135 | 3 | 79 | 53 | 95 | 97 | 2 | 2.11% |
| 28 | B. T. | 1502 | 3 | 79 | 42 | 66 | 64 | -2 | -3.03% |
| 29 | A. G. | 1342 | 3 | 77 | 56 | 73 | 84 | 11 | 15.07% |
| 31 | M. D. | 1124 | 3 | 64 | 46 | 70 | 72 | 2 | 2.86% |
| 32 | R. B. | 1149 | 3 | 58 | 53 | 83 | 85 | 2 | 2.41% |
| 36 | F. H. | 1651 | 3 | 67 | 48 | 91 | 91 | 0 | 0.00% |
| | Mean: | | | 72.7 | 46.9 | 78.25 | 80.50 | 2.25 | 2.88% |
| | Standard deviation: | | | 7.62 | 6.85 | 11.27 | 11.01 | 3.06 | |

TABLE 6

Group 4: Treatment with preparation according to the invention plus treatment with hormones (18 female patients)

| Nr. | Initials | Pat. Nr. | Group | Age | Menopause at | Bone Density in % 1. Measuremt | Bone Density in % 2. Measuremt | Change | Change in % |
|---|---|---|---|---|---|---|---|---|---|
| 1 | E. A. | 1424 | 4 | 56 | 55 | 90 | 90 | 0 | 0.00% |
| 3 | C. F. | 1787 | 4 | 51 | 50 | 72 | 74 | 2 | 2.78% |
| 8 | M. B. | 1938 | 4 | 51 | 50 | 90 | 93 | 3 | 3.33% |
| 10 | H. S. | 1486 | 4 | 57 | 52 | 78 | 78 | 0 | 0.00% |
| 15 | C. S. | 1215 | 4 | 58 | 55 | 65 | 65 | 0 | 0.00% |
| 17 | H. T. | 2061 | 4 | 52 | 41 | 94 | 94 | 0 | 0.00% |
| 19 | I. M. | 2070 | 4 | 54 | 53 | 79 | 81 | 2 | 2.53% |
| 22 | E. S. | 519 | 4 | 46 | 42 | 93 | 97 | 4 | 4.30% |
| 24 | E. G. | 2129 | 4 | 62 | 49 | 63 | 63 | 0 | 0.00% |
| 26 | G. E. | 2144 | 4 | 53 | 51 | 77 | 78 | 1 | 1.30% |
| 30 | A. S. | 2187 | 4 | 74 | 46 | 99 | 100 | 1 | 1.01% |
| 33 | A. H. | 150 | 4 | 54 | 51 | 76 | 76 | 0 | 0.00% |
| 34 | E. E. | 2247 | 4 | 59 | 48 | 79 | 79 | 0 | 0.00% |
| 35 | G. M. | 1594 | 4 | 58 | 54 | 70 | 71 | 1 | 1.43% |
| 37 | M. M. | 2296 | 4 | 56 | 51 | 70 | 72 | 2 | 2.86% |
| 38 | H. E. | 2307 | 4 | 55 | 49 | 79 | 82 | 3 | 3.80% |
| 39 | H. D. | 2302 | 4 | 56 | 54 | 82 | 86 | 4 | 4.88% |
| 40 | W. H. | 2311 | 4 | 52 | 49 | 86 | 87 | 1 | 1.16% |
| | Mean: | | | 55.78 | 50.00 | 80.11 | 81.44 | 1.33 | 1.66% |
| | Standard deviation: | | | 5.83 | 3.96 | 10.22 | 10.65 | 1.41 | |

What is claimed is:

1. A pharmaceutical or dietetic composition comprising: sodium, potassium, magnesium and calcium ions, the sodium and potassium ions being present in the form of at least one of a carbonate or a bicarbonate; at least one enzyme activator; and wherein the composition contains at least 40 mmol of alkaline or alkalizing ions, has a pH of equal to or greater than 7.5 when dissolved in water, and has a quantitative ratio of K:Ca:Na:Mg of 1–10:0.5–8:0.3–5:1.

2. The composition of claim 1, further comprising skeleton substances.

3. The composition of claim 2, wherein the skeleton substances are silicone based.

4. The composition of claim 1, further comprising at least one additive or inactive ingredient.

5. The composition of claim 4, wherein the at least one additive or inactive ingredient is at least one of a carbohydrate or an aromatic.

6. The composition of claim 1, wherein the at least one enzyme activator is selected from the group consisting of Li, Sr, Zn, Fe, Mn, Cu, Cr, Mo, Se, F ions, vitamins, and mixtures thereof.

7. The composition of claim 6, wherein the at least one enzyme activator is selected from the group consisting of vitamin C, vitamin K and vitamin $D_3$.

8. The composition of claim 1, wherein the quantitative ratio of K:Ca:Na:Mg is 5:2.5:1.5:1.

9. The composition of claim 1, wherein the composition has a pH of from 7.5 to 9.5 when dissolved in water.

10. The composition of claim 1, wherein the composition has a pH of from 8.9 to 9.0 when dissolved in water.

11. The composition of claim 1, comprised in a pharmaceutically administrable formulation.

12. The composition of claim 1, comprised in a foodstuff or an additive to a foodstuff.

13. The composition of claim 1, comprised in a medicament.

14. A method for administering a composition to a patient comprising the steps of:
   providing a composition, the composition comprising:
      sodium, potassium, magnesium and calcium ions, the sodium and potassium ions being present in the form of at least one of a carbonate or a bicarbonate;
      at least one enzyme activator;
      wherein the composition contains at least 40 mmol of alkaline or alkalizing ions, has a pH of equal to or greater than 7.5 when dissolved in water, and has a quantitative ratio of K:Ca:Na:Mg of 1–10:0.5–8:0.3–5:1; and administering the composition to a patient.

15. The method of claim 14, wherein the composition is administered to a patient having or at risk of developing acidotic diseases.

16. The method of claim 15, wherein the administration results in inhibition of an acidotic disease.

17. The method of claim 16, wherein the composition is administered to a patient having or at risk of developing osteoporosis.

18. The method of claim 17, wherein the osteoporosis is primary osteoporosis or generalized osteoporosis.

19. The method of claim 17, wherein the administration results in inhibition of osteoporosis.

20. The method of claim 17, wherein the administration stimulates bone formation in the patient, including formation of inorganic and organic bone mass.

21. The method of claim 14, wherein the composition is administered to a patient having a bone fracture or at risk for developing a bone fracture.

22. The method of claim 21, wherein the administration stimulates bone formation in the patient, including formation of inorganic and organic bone mass.

23. The method of claim 16, wherein the composition is administered to a patient having or at risk of developing an ion imbalance.

24. The method of claim 23, wherein the administration restores or maintains ion balance in the patient.

25. The method of claim 14, wherein the composition is administered to a patient having or at risk of developing an ion imbalance in connective tissue of the patient.

26. The method of claim 25, wherein the administration restores or maintains ion balance in connective tissue of the patient.

27. The method of claim 14, wherein the composition is administered to a patient having or at risk of developing reduced bone density.

28. The method of claim 27, wherein the administration stabilizes or improves bone density in the patient.

29. The method of claim 14, wherein said composition is administered to a patient having or at risk of developing reduced organic bone mass and bone mineral density.

30. The method of claim 29, wherein said organic bone mass and bone mineral density is stabilized and improved.

* * * * *

UNITED STATES PATENT AND TRADEMARK OFFICE
CERTIFICATE OF CORRECTION

PATENT NO.    :   5,759,586

DATED         :   June 2, 1998

INVENTOR(S)   :   Fuchs et al.

It is certified that error appears in the above-identified patent and that said Letters Patent is hereby corrected as shown below:

Title page, item [30], delete "[AU] Australia" and insert therefore --[AT] Austria--.

Signed and Sealed this

First Day of September, 1998

*Attest:*

BRUCE LEHMAN

*Attesting Officer*     Commissioner of Patents and Trademarks